United States Patent
Otsuka et al.

(10) Patent No.: US 9,158,037 B2
(45) Date of Patent: Oct. 13, 2015

(54) RESIN MOLDED PRODUCT, METHOD OF MANUFACTURING THE SAME, DIE FOR RESIN MOLDED PRODUCT

(71) Applicant: Olympus Corporation, Tokyo (JP)

(72) Inventors: Yoshitaka Otsuka, Hino (JP); Kazuhiro Kikumori, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 268 days.

(21) Appl. No.: 13/780,320

(22) Filed: Feb. 28, 2013

(65) Prior Publication Data

US 2013/0175720 A1    Jul. 11, 2013

Related U.S. Application Data

(63) Continuation of application No. PCT/JP2011/068305, filed on Aug. 10, 2011.

(30) Foreign Application Priority Data

Sep. 2, 2010    (JP) ................................. 2010-196901

(51) Int. Cl.
*G02B 6/26* (2006.01)
*G02B 1/04* (2006.01)
(Continued)

(52) U.S. Cl.
CPC .............. *G02B 1/041* (2013.01); *A61B 1/0011* (2013.01); *A61B 1/00064* (2013.01); *A61B 1/00096* (2013.01); *B29C 45/16* (2013.01); *B29D 11/005* (2013.01); *B29D 11/0073* (2013.01);
(Continued)

(58) Field of Classification Search
CPC ................... G02B 2003/0093; G02B 6/02052; G02B 6/241; G02B 1/041; G02B 7/022; G02B 23/243; B29D 11/048; B29D 11/0049; A61B 1/00096; A61B 1/0011; B29C 45/16
See application file for complete search history.

(56) References Cited

U.S. PATENT DOCUMENTS 2,559,860 A * 7/1951 Fay ................................ 425/125
3,971,841 A * 7/1976 Rubinstein .................... 264/275
(Continued)

FOREIGN PATENT DOCUMENTS

JP    S62-62541 A    3/1987
JP    9-105871 A    4/1997
(Continued)

OTHER PUBLICATIONS

Supplementary European Search Report issed for corresponding application EP 11 82 1541, mail date May 8, 2014.
(Continued)

*Primary Examiner* — Rhonda Peace
(74) *Attorney, Agent, or Firm* — Arent Fox LLP

(57) ABSTRACT

A resin molded product includes a primary molded object molded by a primary molding die, and a secondary molded object formed to be integrated with the primary molded object by a secondary molding die, the secondary molding die including a shared molding die which shares a part of the primary molding die. The primary molded object includes a rotation regulation portion making a mutual concave-convex fit engagement at a joint portion between the primary molded object and a molding surface of the shared molding die and regulating rotation and shift of the primary molded object in circumferential directions about a center axis of the primary molded object.

16 Claims, 11 Drawing Sheets

(51) Int. Cl.
  *A61B 1/00* (2006.01)
  *B29C 45/16* (2006.01)
  *G02B 23/24* (2006.01)
  *B29D 11/00* (2006.01)
  *G02B 6/42* (2006.01)
  *B29C 45/14* (2006.01)
  *B29L 11/00* (2006.01)

(52) U.S. Cl.
  CPC ..... *G02B23/243* (2013.01); *B29C 2045/14131* (2013.01); *B29K 2995/0025* (2013.01); *B29K 2995/0026* (2013.01); *B29L 2011/0016* (2013.01)

(56) References Cited

U.S. PATENT DOCUMENTS

| | | | | |
|---|---|---|---|---|
| 4,698,089 | A | * | 10/1987 | Matsuzaka et al. ............ 65/290 |
| 6,055,111 | A | * | 4/2000 | Nomura et al. ............... 359/642 |
| 6,129,042 | A | | 10/2000 | Smith et al. |
| 6,144,500 | A | * | 11/2000 | Iwaki et al. .................. 359/719 |
| 6,717,738 | B2 | * | 4/2004 | Yamada et al. ............... 359/642 |
| 8,045,279 | B2 | * | 10/2011 | Kuwa et al. .................. 359/719 |
| 8,305,867 | B2 | * | 11/2012 | Hanashiro et al. ....... 369/112.23 |
| 8,777,847 | B2 | * | 7/2014 | Sato ............................. 600/177 |
| 2006/0012749 | A1 | | 1/2006 | Ai |
| 2010/0214663 | A1 | * | 8/2010 | Yoshioka et al. ............. 359/642 |
| 2010/0220955 | A1 | * | 9/2010 | Mitamura et al. ............. 385/33 |
| 2013/0175720 | A1 | * | 7/2013 | Otsuka et al. ................ 264/1.32 |

FOREIGN PATENT DOCUMENTS

| | | |
|---|---|---|
| JP | 2004-37478 A | 2/2004 |
| JP | 2005-246266 A | 9/2005 |
| JP | 2005-527072 A | 9/2005 |
| JP | 3820137 B2 | 9/2006 |
| JP | 2007-152704 A | 6/2007 |
| JP | 2007-269602 A | 10/2007 |
| JP | 2008-93927 A | 4/2008 |
| JP | 2008-170534 A | 7/2008 |
| JP | 2009-94683 A | 4/2009 |
| JP | 2010-89398 A | 4/2010 |
| JP | 2011-136901 A | 7/2011 |
| WO | WO-03/074251 A1 | 9/2003 |

OTHER PUBLICATIONS

Japanese First Office Action, English Translation, Patent Application No. 2010-196901, Dated Jul. 31, 2014.
International Search Report for PCT/JP2011/068305, date of mailing Sep. 6, 2011.
Notification of Transmittal of Translation of the International Preliminary Report on Patentability issued for PCT/JP2011/068305, date of mailing Mar. 14, 2013.

* cited by examiner

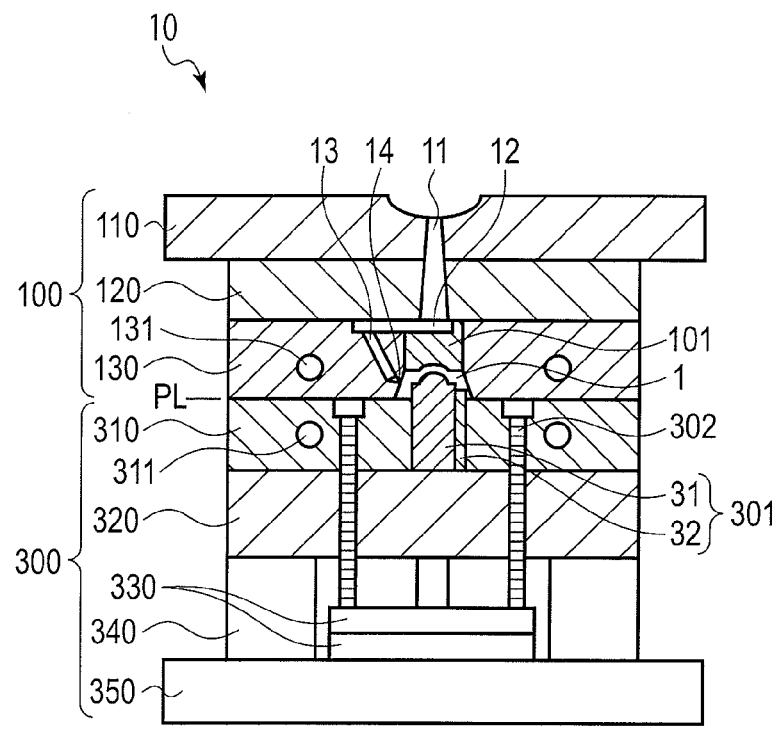
F I G. 6
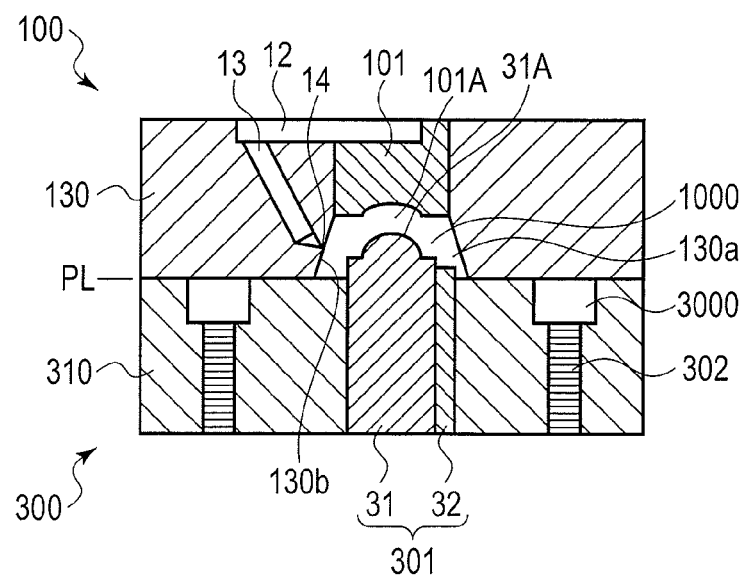
F I G. 7

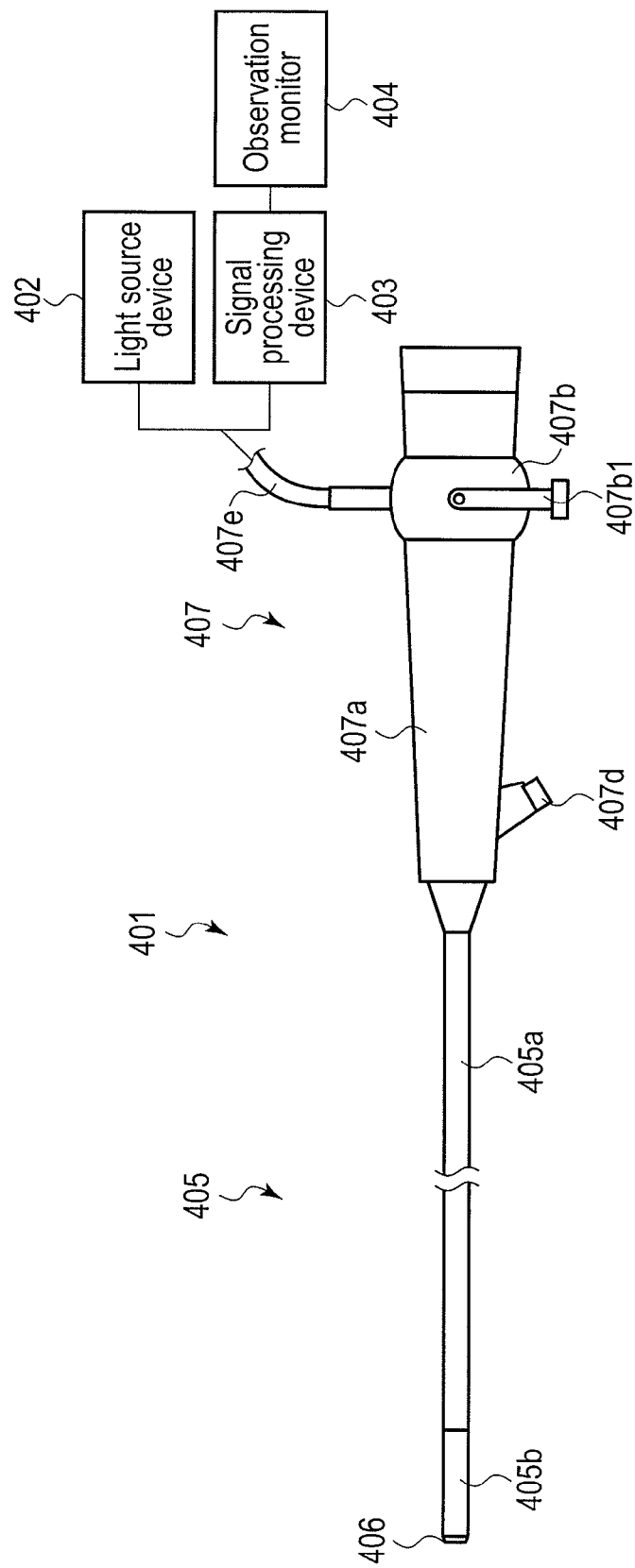
F I G. 14

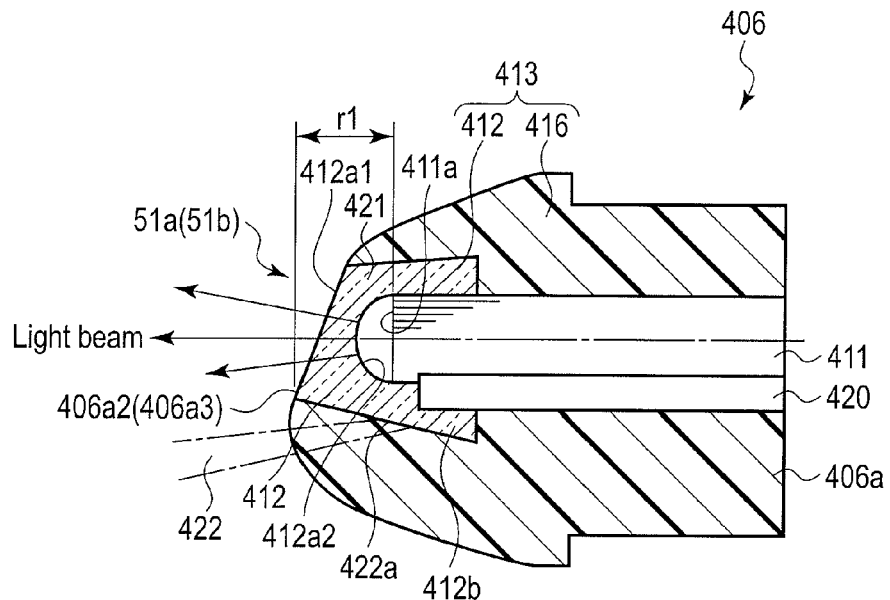
F I G. 17
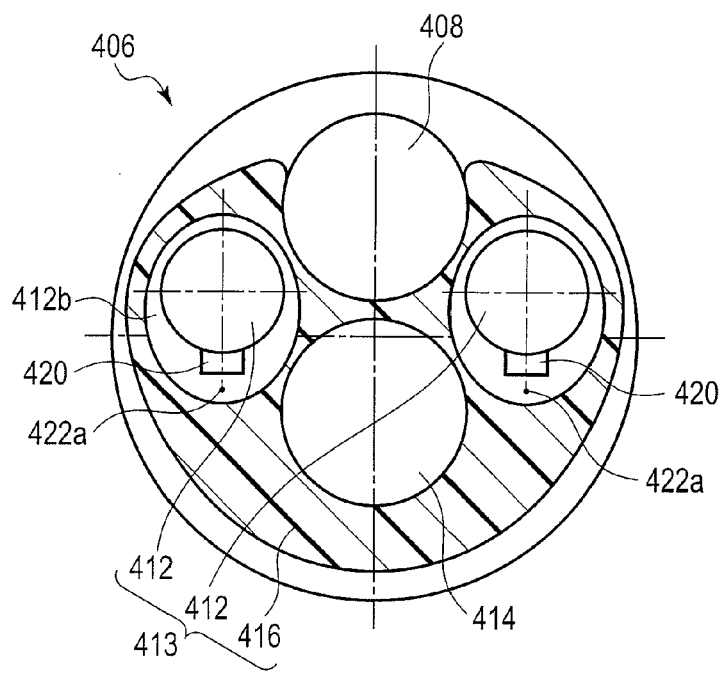
F I G. 18

RESIN MOLDED PRODUCT, METHOD OF MANUFACTURING THE SAME, DIE FOR RESIN MOLDED PRODUCT

CROSS REFERENCE TO RELATED APPLICATIONS

This application is a Continuation Application of PCT Application No. PCT/JP2011/068305, filed Aug. 10, 2011 and based upon and claiming the benefit of priority from prior Japanese Patent Application No. 2010-196901, filed Sep. 2, 2010, the entire contents of all of which are incorporated herein by reference.

BACKGROUND OF THE INVENTION

1. Field of the Invention

The present invention relates to a resin molded product including an optical element used in an observation optical system or an imaging optical system, a manufacturing method of the same, and a die for the resin molded product.

2. Description of the Related Art

In general, a two-color molding technique is used as one of methods of integrally forming an optical element such as a lens and an adjacent member adjacent thereto from a resin material. For example, Japanese Patent No. 3820137 discloses the two-color molding method between an optical element and an adjacent member.

This example uses a metal die for primary molding to primarily mold a primary molded product and a metal die for secondary molding to secondarily mold a secondary molded product. In the metal die for primary molding, a first cavity for a primary molded product is formed by a male metal die and a first female metal die. The same male metal die as the male metal die for the primary molding is used also as the male metal die in the secondary molding. A second cavity for a secondary molded product is formed by the male metal die and the second female metal die. The male metal die includes a fit engagement portion to fitly engage with the molded member (primary molded product).

When molding a two-color molded product, at first, first resin is injected into the first cavity in the metal die for primary-molding described above, to primarily mold the optical element (primary molded product). Thereafter, the male metal die and the first female metal die are separated. At this time, the optical element is fitly engaged in the fit engagement portion of the male metal die. By inserting this male metal die into the second female metal die of the metal die for secondary molding, the second cavity is formed therebetween. A two-color molded product is obtained by secondarily molding an adjacent member connected to an optical element by injecting the second resin into the second cavity.

BRIEF SUMMARY OF THE INVENTION

According to one aspect of the invention, a resin molded product, includes that a primary molded object which is molded by a primary molding die using a first molding material having a light transmissibility, and which has the function of an optical element; and a secondary molded object which is molded by a secondary molding die using a second molding material having a light non-transmissibility, the secondary molding die including a shared molding region shared with the primary molding die and being brought into contact only with an optical element part of the primary molded object, and which is integrated with periphery of the primary molded object, wherein the primary molded object includes a rotation regulation portion which makes a mutual concave-convex fit engagement at a joint portion between the primary molded object and a molding surface of the shared molding die, and which is configured to regulate rotation and shift of the primary molded object in rotation directions about a center axis of the primary molded object.

According to one another aspect of the invention, A resin molded product of an endoscope, includes that an optical member as an optical element which is molded by a primary molding die using a molding material having a light transmissibility; and a distal end forming portion which is molded by a secondary molding die using a different molding material from the molding material, of the optical member, the secondary molding die including at least shared molding die shared with the primary molding die, and which is integrated with the optical member, the distal end forming portion forming a distal end section of the endoscope; wherein the optical member includes a rotation regulation portion which makes a mutual concave-convex fit engagement at a joint portion between the optical member and a molding surface of the shared molding die, and which is configured to regulate a slip of the optical member in rotation directions about a center axis of the optical member.

Further, according to one another aspect of the invention, a method of manufacturing a resin molded product, includes primary molding in which a primary molded object as an optical element is molded by a primary molding die using a molding material, the molding material having a light transmissibility; mold opening in which mold opening of the primary molding die is performed; and secondary molding in which a secondary molded object is molded by a secondary molding die after the mold opening step using a different molding material from the primary molding material, the secondary molding die including at least a shared molding die to be shared with the primary molding die, to thereby integrate the primary molded object and the secondary molded object, wherein the primary molding is performed in a state in which a slip of the primary molded object is regulated in rotation directions about a center axis of the primary molded object by making a mutual concave-convex fit engagement at a joint portion between the primary molded object and a molding surface of the shared molding die, and the secondary molding is performed in a state in which the concave-convex fit engagement is maintained at the joint portion.

Moreover, according to one another aspect of the invention, a molding die for a resin molded product, includes that a primary molding die which is configured to mold a primary molded object as an optical element using a molding material having a light transmissibility, and a secondary molding die which includes at least a shared molding die to be shared with the primary molding die, and which is configured to mold a secondary molded object integrated with the primary molded object using a different molding material from the molding material of the primary molded object, wherein the shared molding die includes a rotation regulation portion forming member which makes a mutual concave-convex fit engagement at a joint portion between the primary molded object and a molding surface of the shared molding die, to thereby regulate a slip of the primary molded object in rotation directions about a center axis of the primary molded object.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 6 is a longitudinal sectional view of a primary-molding metal die in the first embodiment;

FIG. 7 is an enlarged view of a cavity in the primary-molding metal die in the first embodiment;

FIG. 14 is a side view showing a configuration of a whole endoscope according to a second embodiment of the invention;

FIG. 17 is a sectional view taken along a line segment 17-17 in FIG. 15(A); and

FIG. 18 is a sectional view taken along a line segment 18-18 in FIG. 15(B).

DETAILED DESCRIPTION OF THE INVENTION

Hereinafter, embodiments of the invention will be described based on the drawings.

First Embodiment

Configuration

Figure 1:
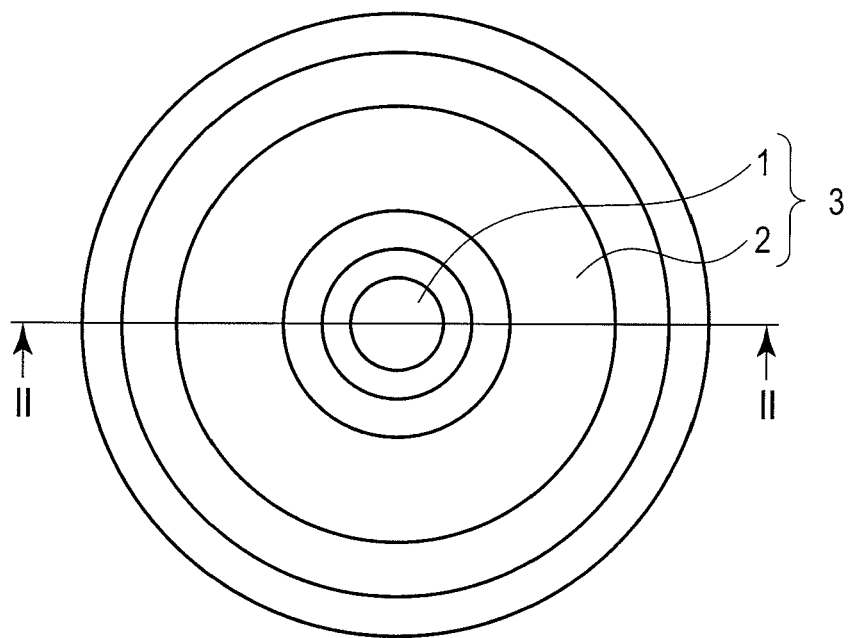
FIG. 1 is a top view of a two-color molded product which is a secondary molded object of a first embodiment of the invention.
Figure 2:
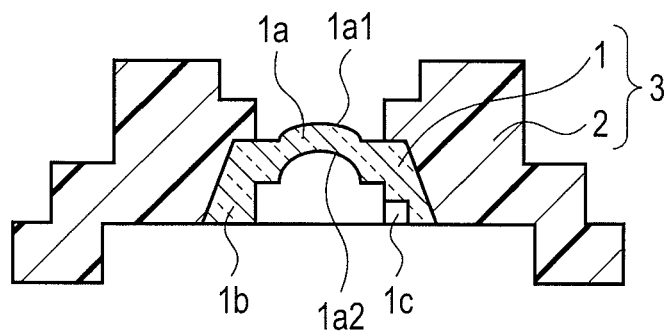
FIG. 2 is a sectional view taken along line II-II in FIG. 1.

FIG. 1 to FIG. 13 show the first embodiment of the invention. FIG. 1 is a top view of a two-color molded product 3 which is a resin molded product in the present embodiment. FIG. 2 is a sectional view taken along line II-II in FIG. 1. FIG. 5 shows a longitudinal section of a whole metal two-color-molding metal die 50 (an example of a die for a resin molded product) to mold the two-color molded product 3.

As shown in FIG. 1 and FIG. 2, the two-color molded product 3 includes an optical element (referred to as a primary molded object) 1, which allows light to transmit, and an adjacent member (referred to as a secondary molded object) 2. The optical element 1 is a lens which is made of a transparent resin material and has, for example, convex and concave shapes. Further, the adjacent member 2 is a cylindrical lens frame which is adjacent to the optical element 1.

As shown in FIG. 2, the optical element 1 includes an optical element body 1a which includes two surfaces (an outer surface and an inner surface) facing each other, and a cylindrical wall portion or skirt 1b having a cylindrical shape and connected to an outer circumferential part of the optical element body 1a. The outer surface of the optical element body 1a is an optically functional convex surface 1a1 having a curved convex shape, and the inner surface is an optically functional concave surface 1a2 having a curved concave shape. The adjacent member 2 is a lens frame used in positioning when the two-color molded product 3 is assembled to an unillustrated component (an observation optical system in an endoscope, or an imaging optical system in a camera). An inner circumferential surface part of the lens frame, that is the adjacent member 2, further includes a structure to assemble a lens which is obtained by any other measure, and, for example, an observation lens unit, an imaging lens unit, an illumination lens unit, a pipe unit, etc., are formed.

Figure 3:
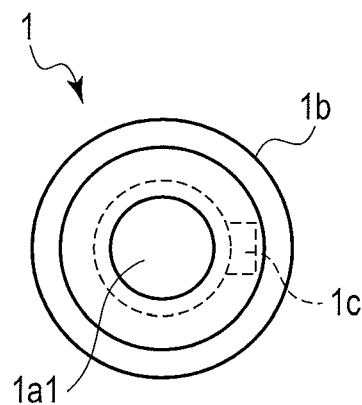
FIG. 3 is a top view showing an optical element which is a primary molded object in the first embodiment.
Figure 4:
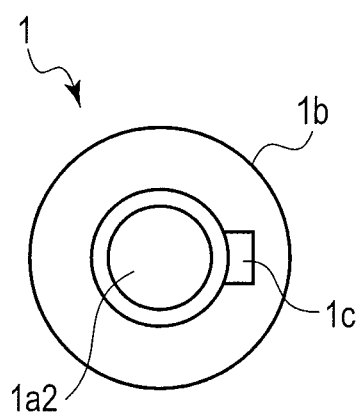
FIG. 4 is a bottom view showing the optical element which is the primary molded object in the first embodiment.
Figure 5:
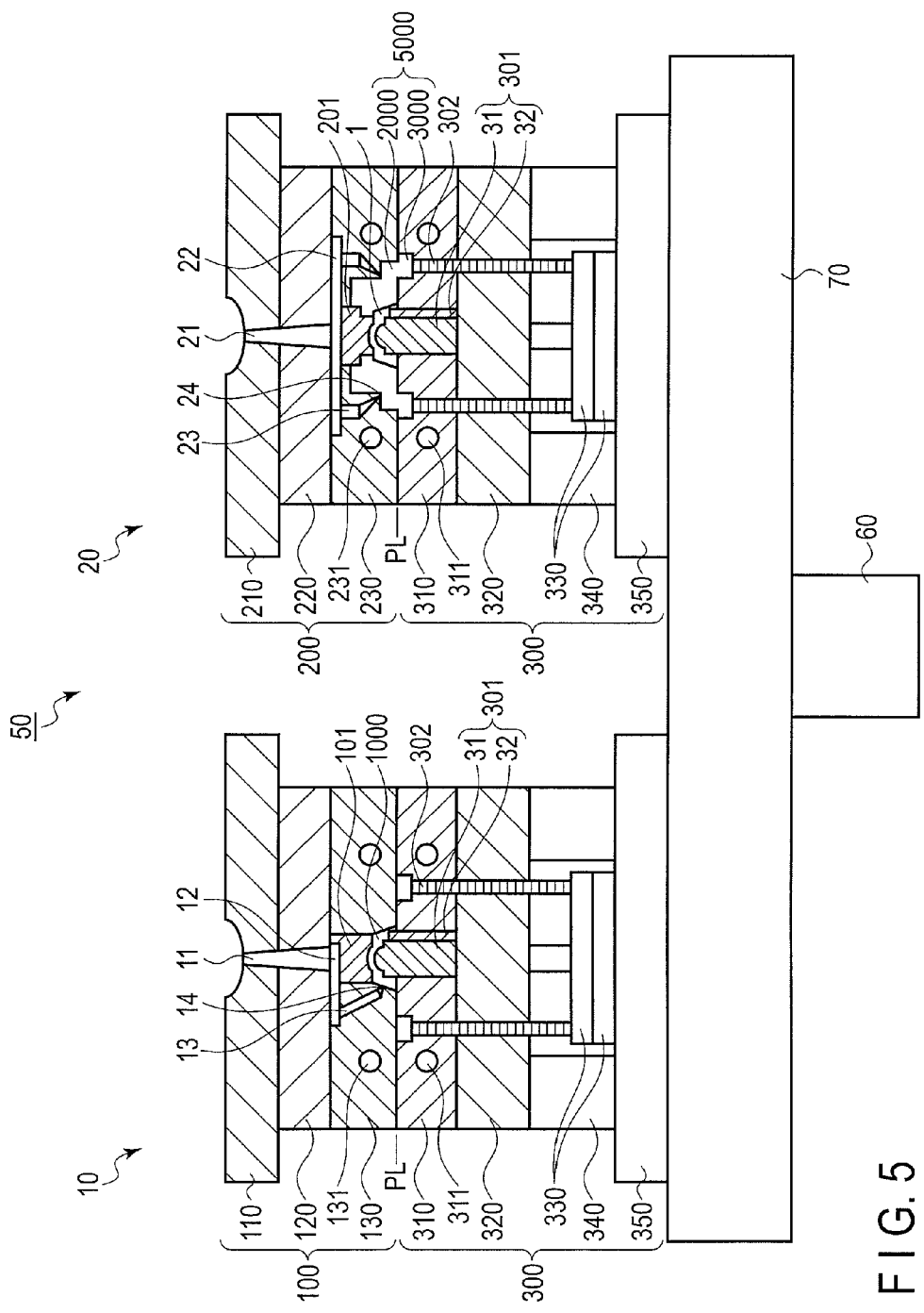
FIG. 5 is a longitudinal sectional view of a whole two-color-molding metal die in the first embodiment.

FIG. 3 shows a top view of the optical element 1, and FIG. 4 shows a bottom view of the optical element 1. The present embodiment has a feature that a rotation regulation portion 1c having a concave shape is provided in the inner circumferential surface of the cylindrical wall portion 1b of the optical element 1, as shown in FIG. 2 and FIG. 4. The rotation regulation portion 1c is formed in the inner circumferential surface of the cylindrical wall portion 1b of the optical element 1 in a concave form and is provided to prevent the optical element 1 from rotating in circumferential directions about (centered on) a center axis of the optical element 1.

Since the rotation regulation portion 1c is provided in the cylindrical wall portion 1b, no shadow thereof hinders optical functions of the optical element 1. The rotation regulation portion 1c is formed by a movable insert 301 described later during primary molding.

Next, a configuration of the two-color-molding metal die 50 according to the present embodiment will be described with reference to FIG. 5. The two-color-molding metal die 50 according to the present embodiment includes a primary-molding metal die (primary molding die) 10 and a secondary-molding metal die (secondary molding die) 20. The primary-molding metal die 10 and secondary-molding metal die 20 are positioned on a movable-side platen 70 of an injection molding machine described later.

The primary-molding metal die 10 includes a primary fixed-side metal die 100 and the movable-side metal die 300 faced (opposed) to each other over a parting line (PL) inserted therebetween. In this example, the primary fixed-side metal die 100 is a first female die, and the movable-side metal die 300 is a male die.

In relation to the primary fixed-side metal die 100, the movable-side metal die 300 is arranged to be movable in opening and closing directions (up and down directions in FIG. 5). The secondary-molding metal die 20 includes a secondary fixed-side metal die 200 and a movable-side metal die 300. The secondary fixed-side metal die 200 is a second female die which is faced (opposed) over a PL, and the movable-side metal die 300 is a male die. In relation to the secondary fixed-side metal die 200, the movable-side metal die 300 is arranged to be movable in the opening and closing directions (up and down directions in FIG. 5).

The primary-molding metal die 10 and the secondary-molding metal die 20 are configured to have different shapes between the primary side and the secondary side in the fixed side, and to have a shape common to the primary side and the secondary side in the movable side. That is, the primary-molding metal die 10 and the secondary-molding metal die 20 share the movable-side metal die 300, as an example of a shared molding die. Therefore, the components forming the movable-side metal dies are not distinguished by names between the primary molding and the secondary molding and the movable-side metal die is hereinafter referred to as the movable-side metal die 300.

After primarily molding the optical element 1 by the primary-molding metal die 10, the optical element 1 is moved to the secondary-molding metal die 20. The adjacent member 2 is secondarily molded to be integral with the optical element 1, to obtain the two-color molded product 3. The primary molding and secondary molding are performed simultaneously and successively, and two-color molded products 3 are accordingly formed sequentially.

Figure 8:
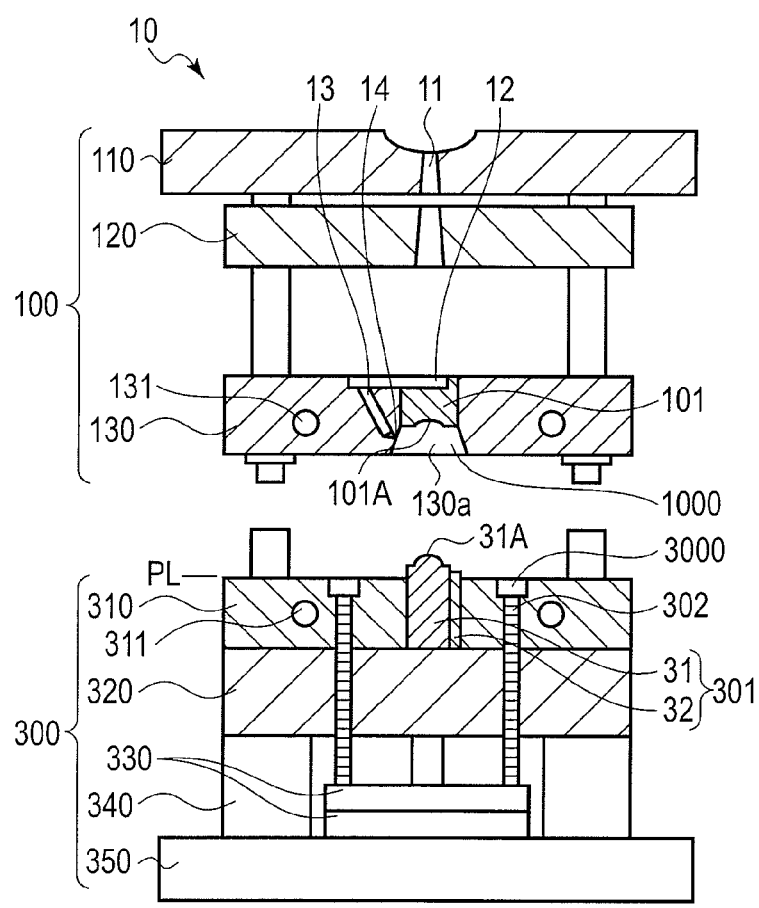
FIG. 8 is a longitudinal sectional view showing a mold opening state of the primary-molding metal die in the first embodiment.
Figure 9:
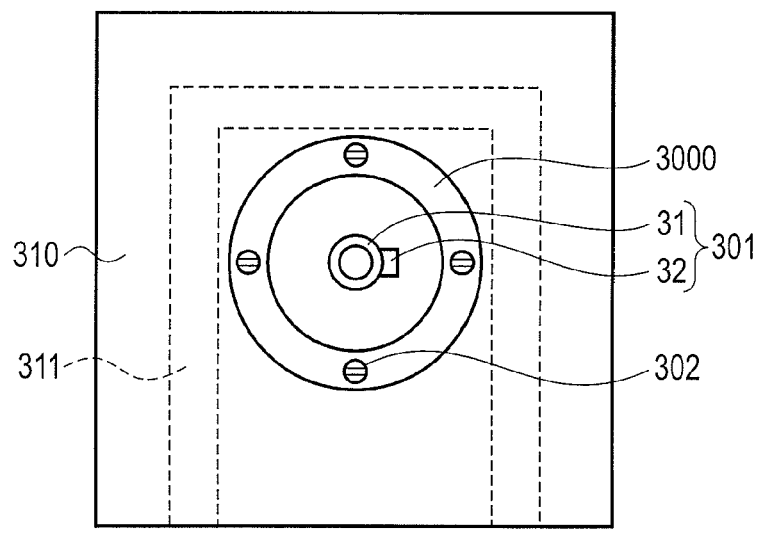
FIG. 9 is a plan view of a movable-side metal die of the primary-molding metal die in the first embodiment.
Figure 10:
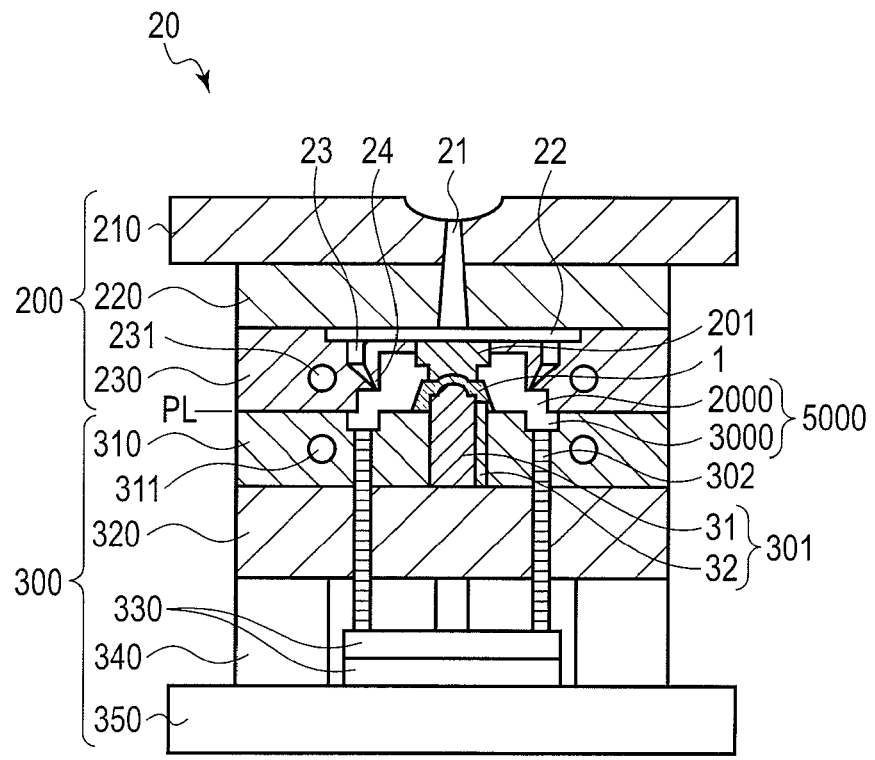
FIG. 10 is a longitudinal sectional view showing a mold clamping state in which the secondary-molding metal die in the first embodiment is clamped.
Figure 11:
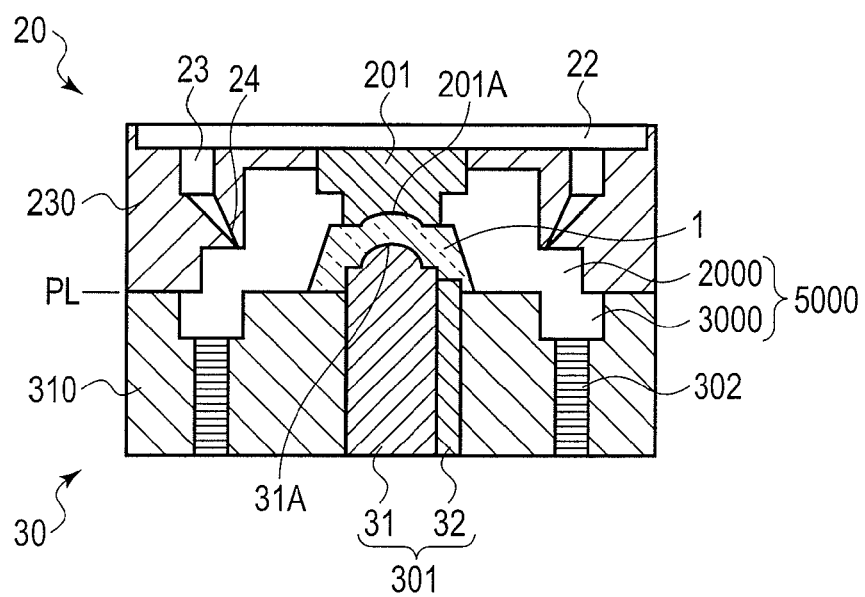
FIG. 11 is a longitudinal sectional view showing a secondary cavity which is formed when the secondary-molding metal die is clamped in the first embodiment.

In the following description, FIG. 6 shows a longitudinal section of the primary-molding metal die. FIG. 7 is an enlarged view of a cavity in the primary-molding metal die. FIG. 8 shows a longitudinal section showing a opened mold state of the metal die for primary molding in the first embodiment. FIG. 9 is a plan view of the movable-side metal die of the primary-molding metal die in the first embodiment. FIG. 10 shows a longitudinal section showing a clamped mold state of the secondary-molding metal die.

As shown in FIG. 6, the primary fixed-side metal die 100 includes a primary fixed-side attachment plate 110, a primary fixed-side fall plate 120, and a primary fixed-side die plate 130. The primary fixed insert 101 is fitly inserted in a center part of the primary fixed-side mold plate 130.

The movable-side metal die 300, which is faced to the primary fixed-side metal die 100, includes a movable-side mold plate 310, a movable-side receive plate 320, a spacer block 340, and a movable-side attachment plate 350. Inside the spacer block 340, an ejector plate 330 which forms an ejection mechanism is provided. Four ejector pins 302 are attached to the ejector plate 330 (FIG. 9). A movable insert 301 is fitly inserted in a center part of the movable-side mold plate 310. That is, the movable insert 301 is inserted into the movable-side metal die 300. The movable insert 301 is arranged to be faced (opposed) to the primary fixed insert 101 with being spaced.

As shown in FIG. 10, the secondary fixed-side metal die 200 includes a secondary fixed-side attachment plate 210, a secondary fixed-side fall plate 220, and a secondary fixed-side die plate 230. A secondary fixed insert 201 is fitly inserted in the secondary fixed-side mold plate 230. The movable-side metal die 300, which is faced to the secondary fixed-side metal die 200, has the same configuration as the movable-side metal die 300 described above.

The movable side attachment plate 350 of the primary-molding metal die 10 and the movable-side attachment plate 350 of the secondary-molding metal die 20 are fixed to the movable-side platen 70 of the same injection molding machine.

This movable side platen 70 is movable in a mold opening direction. A rotation shaft 60 parallel to the mold opening direction is provided at a center position of the movable side platen 70. The movable side platen 70 is rotatable about (centered on) this revolving shaft 60. Further, the primary fixed-side attachment plate 110 and the secondary fixed-side attachment plate 210 are fixed to the fixed-side platen of the injection molding machine, though not shown.

Next, a detailed structure of the primary-molding metal die 10 will described.

FIG. 7 shows a state in which the movable-side die plate 310 and the primary fixed-side die plate 130 are brought into contact with each other in the primary-molding metal die 10. FIG. 8 shows a mold opening state of the primarily molding metal die 10.

A concave area 130*a* configured to form a primary cavity is provided in an approximate center of a lower surface of the primary fixed-side mold plate 130. An upper end surface of this concave area 130*a* is formed of a lower (under) surface of the primary fixed insert 101. On the lower surface of this primary fixed insert 101, a primary fixed-side molding surface 101A having a concave curved shape is exposed. This primary fixed-side molding surface 101A molds the optically functional convex surface 1*a*1 of the optical element 1 having a convex curved shape. Further, a molding surface 130*b*, which molds the outer side surface shape of the cylindrical wall part 1*b* of the optical element 1, is formed in the primary fixed-side mold plate 130.

Further, the movable insert 301 is arranged on the movable-side die plate 310 so as to be apart from and faced to the primary fixed insert 101 when the movable insert 301 is brought into contact with the primary fixed-side die plate 130. This movable insert 301 includes a cylindrical insert body 31 and a rotation-regulation-portion forming member 32 used as a male convex portion. The rotation-regulation-portion forming member 32 is a part of the movable insert 301.

A movable-side molding surface 31A having a convex curved shape is formed on an upper surface of the insert body 31 of the movable insert 301. This movable-side molding surface 31A molds the optically functional concave surface 1*a*2 of the optical element 1 having a concave curved shape.

Further, the rotation-regulation-portion forming member 32 is arranged to be protruded from a part of a molding surface of a male die, which is the outer circumferential surface of the movable insert 301, in circumferential directions. By this rotation-regulation-portion forming member 32, the rotation regulation portion 1*c* is molded on the inner circumferential surface of the cylindrical wall portion 1*b* of the optical element 1 to form a concave portion.

Further, during mold clamping in which the primary fixed-side metal die 100 and the movable-side metal die 300 are brought into contact with each other (FIGS. 5 to 7), a primary molding cavity 1000 is formed in a sealing space defined by the molding surface 130*b*, the primary fixed-side molding surface 101A, and the movable-side molding surface 31A. The primary molding cavity 1000 is formed in the optically functional convex surface 1*a*1, the optically functional concave surface 1*a*2, and the rotation regulation portion 1*c* of the optical element 1. At the same time, the outer circumferential surface of the cylindrical wall portion 1*b* of the optical element 1 is formed by the molding surface 130*b*. In addition, a primary sprue 11 for primary molding which supplies a molten material for the optical element 1 toward the mold opening direction is formed at a central position of each of the primary fixed-side attachment plate 110 and the primary fixed-side fall plate 120.

Further, the primary fixed-side die plate 130 is provided with a primary molding runner 12, a secondary sprue 13 for primary molding, and a pin point gate 14 for primary molding (FIG. 6). The primary molding cavity 1000 is filled with the molten material for the optical element 1 through each portion of the primary fixed-side die plate 130 from the primary sprue 11 for primary molding. A primary fixed-side temperature control tube 131 is provided to the primary fixed-side die plate 130. In this primary fixed-side temperature control tube 131, a medium such as water or oil, the temperature of which is controlled, flows constantly during molding.

Further, a movable-side space 3000 for forming a part of a secondary molding cavity is formed at an outer peripheral portion of the movable insert 301 in a side thereof facing the PL, to be coaxial with the center of a die axis of the movable-side die plate 310, in the movable-side die plate 310. Four ejector pins 302 are provided to be in contact with a bottom surface of the movable-side space 3000 (FIG. 9).

Next, a structure of the secondary-molding metal die 20 will be described in details.

Figure 12:
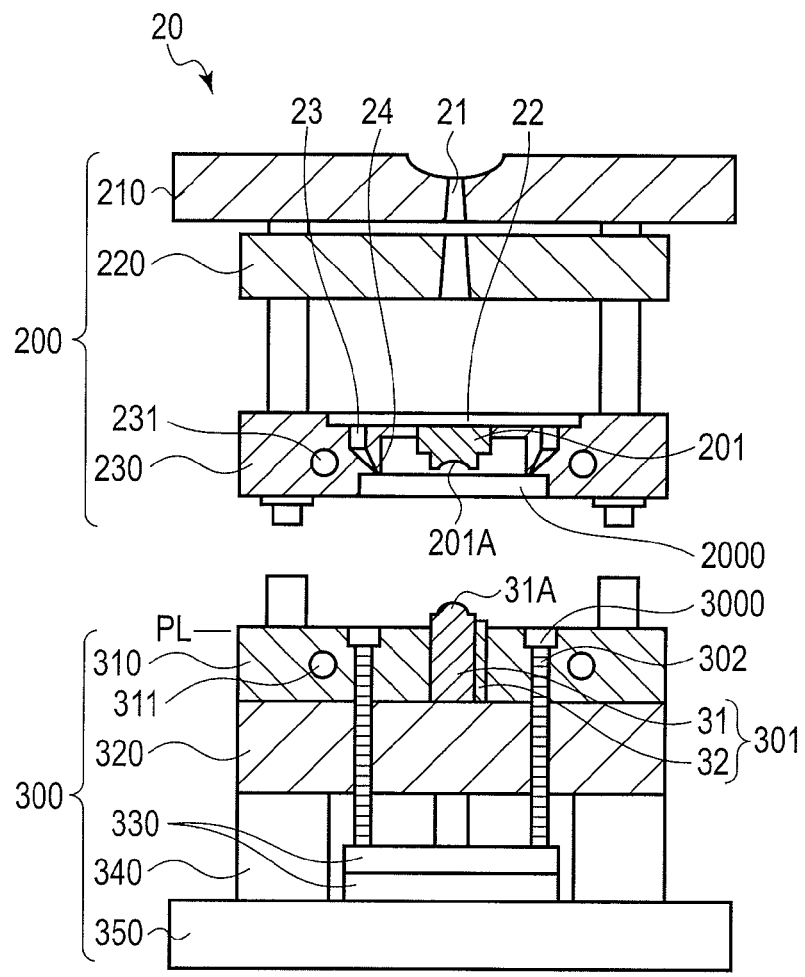
FIG. 12 is a longitudinal sectional view showing a mold opening state in which the secondary-molding metal die in the first embodiment is opened.

FIG. 12 shows a mold opening state of the secondary-molding metal die 20. A secondary fixed-side space 2000 configured to form a secondary molded-object cavity is formed in the lower surface of the secondary fixed-side die plate 230 of the secondary fixed-side metal die 200.

At a central part of this secondary fixed-side space 2000, the secondary fixed insert 201 is provided to protrude downward. A secondary fixed-side molding surface 201A having the same concave curved shape as the primary fixed insert 101 is formed in the lower surface of the secondary fixed insert 201.

Further, a molding space for secondarily molding the adjacent member 2 between the circumferential wall portion of the secondary fixed side space 2000 and the secondary fixed insert 201 is formed in the lower surface of the secondary fixed-side die plate 230. As shown in FIG. 10, when the movable-side metal die 300 and the secondary fixed-side metal die 200 are subjected to mold clamping, a secondary molding cavity 5000 in which the secondary fixed-side space 2000 communicates with the movable side space 3000 is formed.

Also as shown in FIG. 10, a primary sprue 21 for secondary molding to supply a molten material for the adjacent member 2 toward the mold opening direction is formed at the central position of each of the secondary fixed-side attachment plate 210 and the secondary fixed-side fall plate 220.

Further, a pin point gate 24 for secondary molding for filling resin in the secondary fixed-side space 2000 and the movable-side space 3000, which form a secondary molding cavity, sequentially through the runner 22 for secondary molding and the secondary sprue 23 for secondary molding is provided in the secondary fixed side die plate 230. At first, the secondary-molding metal die 20 uses the optical element 1 which has been primarily molded by the primary-molding metal die 10, and which is held by the movable-side metal die 300.

The secondary fixed-side metal die 200 of the secondary-molding metal die 20 is subjected to mold clamping with the movable-side metal die 300 in which the optical element 1 is held. In this mold clamping, the optical element 1 is set between the secondary fixed-side metal die 200 and the movable-side metal die 300, i.e., the inside of the secondary molding cavity 5000.

Next, manufacturing method of the primary-molding metal die 3 will described.

When the two-color molded product 3 is manufactured from the resin material of present embodiment, the two-color-molding metal die 50 of FIG. 5 is used.

The two-color-molding metal die 50 primarily molds the optical element 1 by the primary fixed-side metal die 100. Subsequently, the adjacent member 2 which is melted to integrally fit the circumference of the optical element 1 is secondarily molded by the secondary-molding metal die 20, to thereby form the two-color molded product 3.

Firstly, in molding the optical element 1 (primary molding step), the molten material for the optical element 1 is supplied from an unillustrated resin injection unit to a primary sprue 11 with which the primary fixed-side attachment plate 110 and the primary fixed-side fall plate 120 communicate.

As shown in FIG. 6, this molten material passes from the primary sprue 11 through the primary molding runner 12 of the primary fixed-side die plate 130 and the secondary sprue 13 for primary molding, and further through the pin point gate 14 for primary molding, and is filled in the primary molding cavity 1000. In addition, the resin material of the optical element 1 is selected from common transparent resin, such as polycarbonate (PC), for example.

Subsequently, a pressed state is maintained only for a predetermined period with a predetermined pressure to the resin filled in the primary molding cavity 1000. Subsequently, the optical element 1 which is a primary molded object is obtained by cooling the filled resin in the primary molding cavity 1000.

At this time, the rotation regulation portion 1c as a concave portion is molded at a part of the inner circumferential surface of the cylindrical wall portion 1b of the molded optical element 1, which makes contact with the rotation-regulation-portion forming member 32, as shown in FIG. 7. At this time, the rotation regulation portion 1c is held in concave-convex fit engagement with the rotation-regulation-portion forming member 32.

Figure 13:
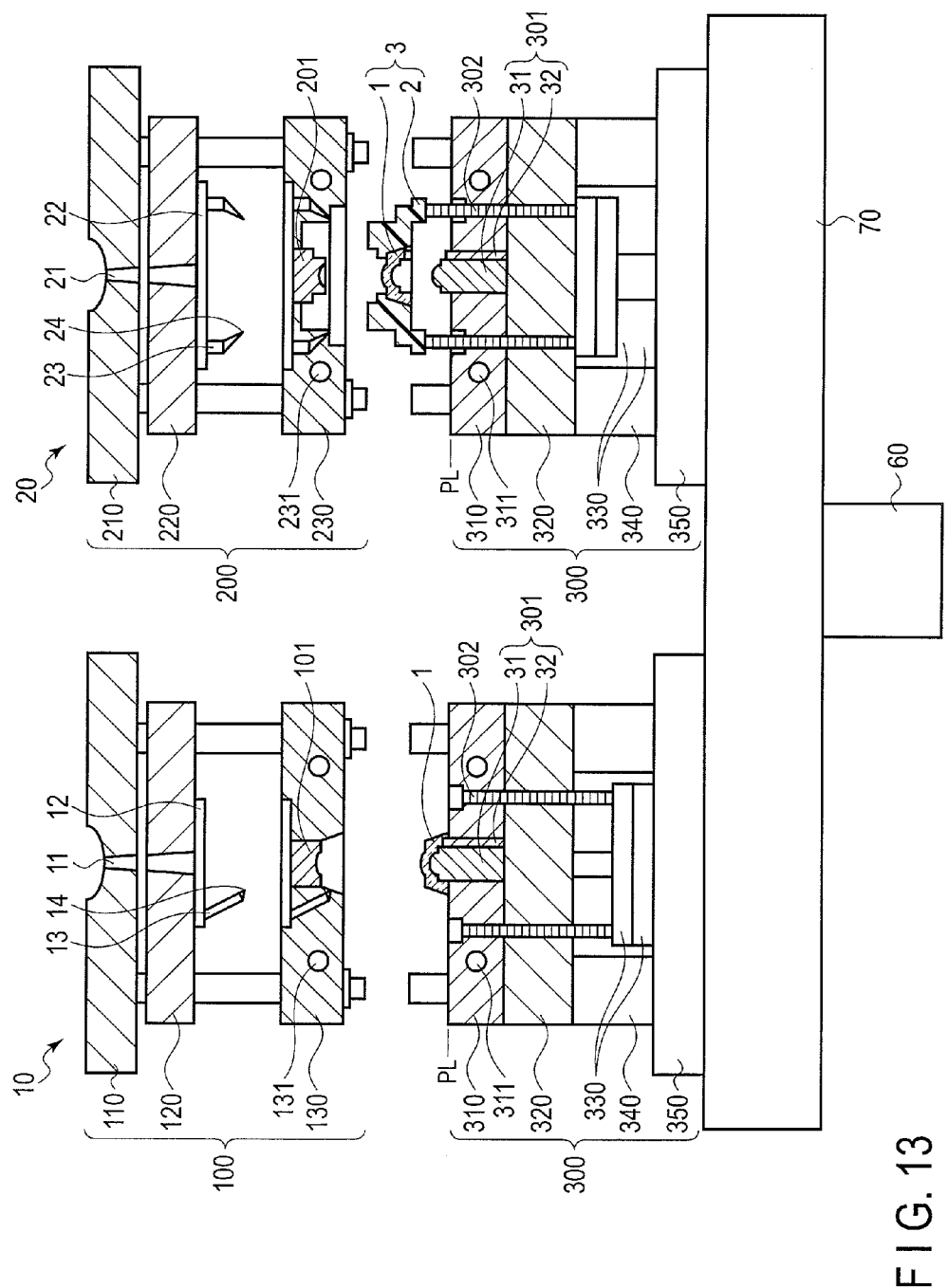
FIG. 13 is a longitudinal sectional view showing a mold opening state of the whole metal two-color-molding metal die after completion of molding in the first embodiment.
Figure 15:
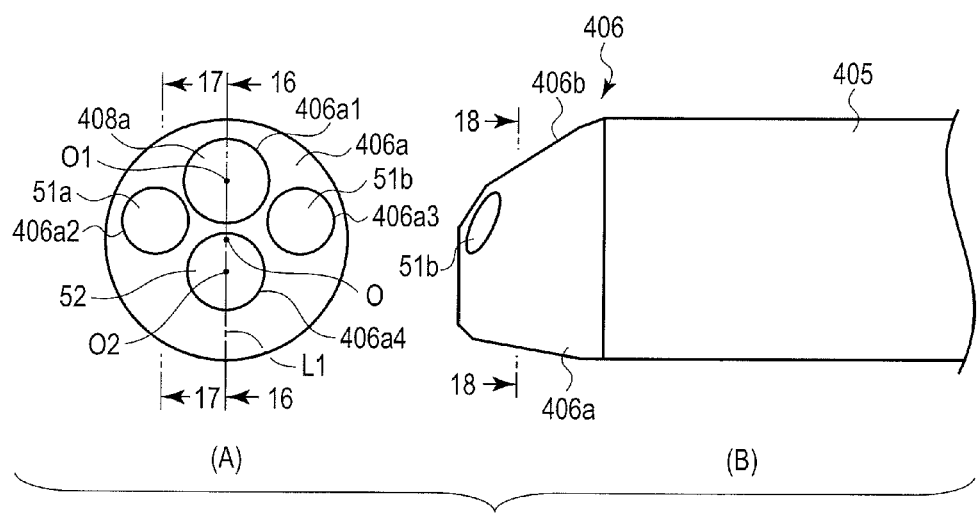
FIG. 15 shows a distal end section of the endoscope according to the second embodiment, in which (A) is a schematic diagram and (B) is a side view.

Thereafter, as shown in FIG. 13, the movable-side metal die 300 is moved in a direction away from the primary fixed-side metal die 100 and the secondary fixed-side metal die 200, thus performing the mold opening (mold opening process).

At this time, as shown in FIG. 13, the optical element 1 is held on the movable insert 301 by cooling shrink of the filled resin. The optical element 1 and the secondary sprue 13 are separated at the position of the primary-molding pin point gate 14 simultaneously with mold opening.

Next, the movable-side platen 70 of the molding machine is rotated by 180 degrees, about the rotation shaft 60, maintaining the optical element 1 by the movable insert 301. By this rotation, the movable-side metal die 300 on the side where the optical element 1 is held and the secondary fixed-side metal die 200 are faced to each other. Simultaneously, the movable-side metal die 300 on the side where the previously manufactured optical element 1 has been pulled off and the secondary fixed side metal die 100 are faced to each other.

The metal die is closed in this faced (opposed) state. At this time, as shown in FIG. 10, the optically functional convex surface 1a1 of the optical element 1 is brought into tight contact with the secondary fixed-side molding surface 201A of the secondary fixed insert 201. In this state, the secondary fixed-side space 2000 and the movable-side space 3000 are made communicate with each other, and the secondary molding cavity 5000 to which periphery of the optical element 1 is exposed is formed.

Subsequently, secondary molding process is performed.

As shown in FIG. 10, colored resin is filled in the secondary molding cavity 5000, and is maintained in a state that the filled resin is pressed with a predetermined pressure for a predetermined time period. Thereafter, in this pressed state, the adjacent member 2 is formed by cooling the resin.

At this time, the optical element 1 and the adjacent member 2 are bonded and integrated together to form the two-color molded product 3. The resin material of the adjacent member 2 is, for example, a common colored resin material such as polycarbonate (PC). By the secondary-molding metal die 20 and the primary-molding metal die 10, the secondary molding and primary molding are performed simultaneously in parallel, to manufacture the two-color molded product 3 and the optical element 1.

Subsequently, as shown in FIG. 13, the secondary fixed-side metal die 200 and the movable-side metal die 300 are subjected to mold opening. At this time, the two-color molded product 3 in the movable-side metal die 300 of the secondary-molding metal die 20 can be taken off by separating the secondary sprue 23 at the secondary-molding pin point gate 24 and by projecting the ejector pins 302 by the ejection mechanism of the molding machine.

At the same time when this secondary-molding metal die 20 is subjected to mold opening, the primary-molding metal die 10 is also subjected to mold opening, and the new optical element 1 is thereby molded. Subsequently, a series of primary molding process and secondary molding process described above are repeated.

(Function)

Next, function of the configuration described above will be described.

In the present embodiment, the rotation regulation portion 1c having a concave shape is molded when the optical element 1 is formed. The optical element 1 is hard to take off from the movable insert 301 at the time of setting to the secondary fixed-side metal die 200 after the mold opening of the primary-molding metal die 10 because the rotation regulation portion 1c and the rotation-regulation-portion forming member 32 are fitly engaged with each other. The optical element 1 is set in the secondary fixed-side metal die 200, with being maintained in the movable insert 301.

Further, in the secondary fixed-side metal die 200, the rotation regulation portion 1c and the rotation-regulation-portion forming member 32 are fitly engaged with each other. Therefore, when the molten resin for the secondary molding is filled, the optical element 1 is prevented from being rotated in the circumferential directions and from being sifted in the surface directions.

(Effect)

According to the configuration described above, the following effects are produced.

According to the present embodiment, the rotation regulation portion 1c formed during primary molding of the optical element 1 prevents rotation in the circumferential directions of the optical element 1 by the injection pressure of molten resin during secondary molding.

Owing to this prevention of rotation, the two-color molded product 3 in which the adjacent member 2 is uniformly formed in the periphery of the optical element 1 can be provided without degrading the performance of the optical element 1 during the secondary molding, even if the optical element 1 forms a disc shape.

Therefore, the two-color molded product 3 is obtained with improved stability against dimensional errors of the optical element 1 and the adjacent member 2 which are integrated with high precision.

Further, insofar as the rotation regulation portion 1c has a size which can sufficiently withstand the injection pressure of the molten material at least in the second molding, appropriate modifications may be made, for example, by forming the rotation regulation portion 1c to have a semicircular shape, increasing the number of the rotation regulation portions 1c, and/or performing pressure dispersion.

Further, the present embodiment discloses, as an example, the rotation regulation portion 1c of the optical element 1 which has a concave shape but is not limited to this shape. For example, the inner circumferential shape of the cylindrical wall portion 1b of the optical element 1 as the rotation regulation portion 1c may be modified into a shape, such as a rectangle or a triangle, which is not symmetrical about its rotation axis. Accordingly, the rotation regulation portion 1c is not limited to the rotation regulation portion 1c according to the first embodiment but the shape of the rotation regulation portion 1c may be changed arbitrarily as needed.

Second Embodiment

Configuration

FIG. 14 to FIG. 18 show the second embodiment of the invention.

Figure 16:
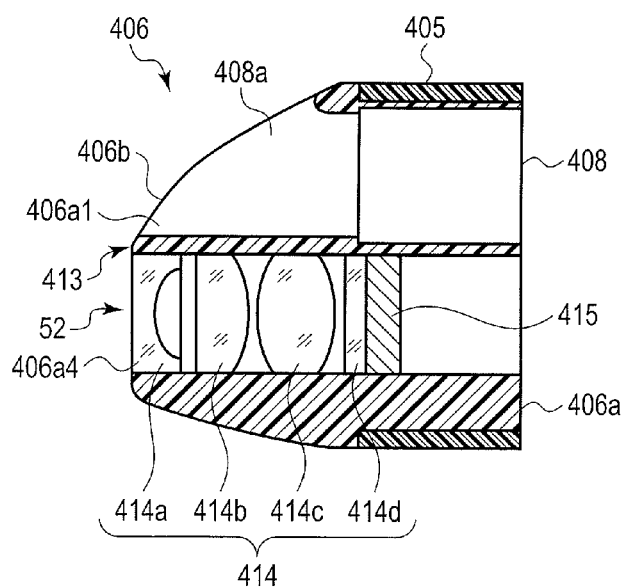
FIG. 16 is a sectional view taken along a line segment 16-16 in FIG. 15(A)

FIG. 14 is a side view showing a configuration of a whole endoscope according to the second embodiment of the invention. FIG. 15(A) shows a distal end section of the endoscope according to the second embodiment, and FIG. 15(B) shows a side view of the distal end section of the endoscope. FIG. 16 is a sectional view taken along a line segment 16-16 in FIG. 15(A). FIG. 17 is a sectional view taken along a line segment 17-17 in FIG. 15(A). FIG. 18 is a sectional view taken along a line segment 18-18 in FIG. 15(B).

In the present embodiment, the invention is applied to a distal end section 406 of an endoscope 401. FIG. 14 shows a configuration of the whole endoscope 401 with which inside of a body cavity is observed, diagnosed, treated, etc. The endoscope 401 includes an elongate and flexible insertion section 405 which is configured to be inserted into a patient's body cavity. A hard distal end section 406 is provided at a distal end of the insertion section 405, and an operation section 407 is provided at a proximal end of the insertion section 405.

The elongate insertion section 405 is formed by connecting a flexible tube section 405a, a bending section 405b, and the distal end section 406. The bending section 405b is connected at a distal end of the flexible tube section 405a. The distal end section 406 is connected to a distal end of the bending section 405b.

The bending section 405b is configured, for example, in a manner that a plurality of unillustrated rods are arranged along center axial directions (longitudinal axial directions) of the insertion section 405, and each of adjacent rods are pivotally attached to one another by axle member so as to pivot in the up-and-down directions. In this manner, the bending section 405b may be configured to be only two-directionally bendable in the up-and-down directions. The bending section 405b may be configured to be four-directionally bendable with being bendable not only in the up-and-down directions but also in the left-and-right directions.

The operation section 407 includes a grip portion 407a and a bending mechanism portion 407b. Further, in case of a fiberscope which uses an image guide, an unillustrated ocular portion is provided at a proximal (tail) end portion of the operation section 407. The bending mechanism portion 407b is provided with a bending operation knob 407b1 of a lever type.

By pivoting the bending operation knob 407b1 of the operation section 407, the bendable section 405b is forced to bend only in the up-and-down directions to change the facing direction of the distal end section 406. Further, the grip portion 407a is provided with a metal channel cap 407d.

One end of the universal code 407e is connected to a side face of the bending mechanism portion 407b. The other end of this universal code 407e is provided with an unillustrated scope connector. The endoscope 401 is connected to a light source device 402 and a signal processing device 403 through the scope connector. An observation monitor 404 is connected to the signal processing device 403.

As shown in FIGS. 15(A)(B) and FIG. 16, the distal end section 406 of the insertion unit 405 includes the distal end section body (distal end forming part) 406a as a single component. This distal end section body 406a is integrally molded from resin. Resin of a material which forms the distal end section body 406a is formed from optically opaque resin, for example, black resin such as polycarbonate (PC).

As shown in FIG. 15(A), two lighting window sections 51a and 51b configured to emit illumination light, an observation window section 52, and a distal opening 408a of a channel 408 for inserting a treatment instrument are provided in a distal surface of the distal end section body 406a.

In present embodiment, in FIG. 15(A), the distal opening 408a of the channel 408 for inserting the treatment instrument is provided to an upper side in relation to a center position O of the distal surface of the distal end section body 406a, as well as the observation window section 52 to a lower side thereof. The two lighting window sections 51a and 51b are arranged in leftward-and-rightward symmetrical positions with respect to each other relative to a reference line L1 which connects a center axis O1 of the distal opening 408a and a center axis O2 of the observation window section 52, respectively.

Further, a tapered slope 406b which is tapered as it goes toward the distal side (a side of the channel 408 toward the distal opening 408a) is formed in the outer circumferential surface of the distal end section body 406a on the side of the upper surface in FIG. 15(B). In this manner, the distal surface of the distal end section body 406a has a flat shape which is greater in leftward-and-rightward and shorter in upward-and-downward, for example, a paddle-like portion having an approximately elliptical shape which has a shorter axis in the up-and-down directions and a longer axis in the left-and-right directions. The circumferential surface of the distal end section body 406a is formed of a smooth surface without a sharp jag or great unevenness from an edge of the distal surface to an outer circumference of a rear end portion of the distal end section body 406a.

Specifically, the entire thereof is formed of a curved continuous surface from the edge of an approximately elliptical distal surface to an approximately circular outer circumferential surface of a rear proximal end part of the distal end section body 406a. The outer circumferential surface of the distal end section body 406a is a smooth curved surface which transits from an approximately elliptical shape to an approximately circular shape, in a range from the edge of the distal surface having the approximately elliptical shape to the bending section 405b having the approximately circular cross section, which is provided to be adjacent to the proximal end of the distal end section 406.

As shown in FIG. 16, the slope 406b on the side of the upper surface of the distal end section body 406a is positioned to a side of a direction in which the bending section 405b bends, i.e., to a side in which the distal end section 406 rises up. A circumferential edge of the distal surface of the distal end section body 406a and corner parts of the distal end section body 406a exposed to outside each are rounded edges.

As shown in FIG. 15(A), four holes (406a1 to 406a4) are formed inside the distal end section body 406a, in parallel with the axial directions of the insertion section 405. A distal opening 408a of the channel 408 is formed in the first hole 406a1. A pair of right and left illumination holes in which attachment members for illumination optical systems are set are formed in the second hole 406a2 and the third hole 406a3.

An observation hole in which attachment member for an observation optical system is set is formed in the fourth hole 406a4.

An unillustrated channel tube is connected through a metal connection cap to an inner end of the first hole (channel hole) 406a1 that forms the distal opening 408a of the channel 408. A proximal (backward) end part of this channel tube is guided to the operation section 407 through inside of the bending section 405b and a flexible tube section 405a, and is connected to the metal channel cap 407d. The channel 408 which penetrates from the metal channel cap 407d to the distal opening 408a of the distal end section 406 is formed. This channel 408 is used not only to insert a treatment instrument but also to supply air/water.

As shown in FIG. 16, an attachment member for the observation optical system is set in the fourth hole (observation hole) 406a4. A first lens (or cover glass) 414a which forms the observation window section 52 is provided at the most distal position of the fourth hole (observation hole) 406a4.

To the proximal side (behind) this first lens 414a, the second lens 414b, the third lens 414c, and the fourth lens 414d are provided sequentially, thereby forming the observation optical system 414. This observation optical system 414 is fixed to the inner circumferential wall surface of the fourth hole 406a4 of the distal end section body 406a by, for example, an adhesive agent. At an image forming position of the observation optical system 414, an image element section 415 which includes an image element such as a CCD is provided.

An observation image image-formed by the observation optical system 414 is converted into an electric signal through photoelectric conversion by the image element section 415, and is transmitted to the signal processing device 403 through an unillustrated signal cable. The signal processing device 403 converts the electrical signal into a video signal, and displays an image on the observation monitor 404. In place of the image element section 415, a distal end of an image guide fiber may be configured to be fixed. In this case, the observation image image-formed by the observation optical system 414 is guided to the ocular portion (part) through the image guide fiber, and the observation image is observed by the ocular.

As shown in FIG. 17, an illumination lens 412 which forms the lighting window sections 51a and 51b is provided in the second hole (illumination storage hole) 406a2 and the third hole (illumination storage hole) 406a3 of the distal end section body 406a at the most distal position.

In the present embodiment, the two-color molded product 413 is formed in which the illumination lens 412 as an example of an optical member and the distal end section body 406a as a support member 416 thereof are integrally molded.

The illumination lens 412 of the two-color molded product 413 in the present embodiment is formed from an optically transparent resin material, for example, polycarbonate (PC). The support member 416 is formed from optically opaque, for example, black resin, such as polycarbonate (PC).

Further, these members are integrally formed by injection molding of two-color molding, i.e., through a molding process by which the distal end section body 406a as the support member 416 is secondarily molded after the illumination lens 412 is primarily molded. Since the support member 416 is optically opaque, unnecessary light is prevented from scattering from the outer circumferential portion of the illumination lens 412.

In addition, as shown in FIG. 17 and FIG. 18, in the present embodiment, the illumination lens 412 includes a lens body 412a having an approximately circular shape, and a cylindrical wall portion 412b having a cylindrical shape and connected to an outer circumferential part of this lens body 412a. An outer surface of the lens body 412a is an optically functional surface 412a1 having a slope shape, and an inner surface thereof is an optically functional concave surface 412a2 having a curved concave shape. A concave rotation-regulation portion 420 is provided in the inner circumferential surface of the cylindrical wall portion 412b of the lens body 412a. Further, a rotation regulation portion 420 of the illumination lens 412 is formed as a primary molded object 421 through a primary molding process by the unillustrated primary-molding metal die.

The rotation regulation portion 420 is positioned on an inner circumferential surface of the cylindrical wall portion 412b of the illumination lens 412, as shown in FIG. 18, along axial directions of the distal end section body 406a, as shown in FIG. 17, except an optically effective range r1 of the illumination lens 412. That is, the rotation regulation portion 420 is provided to extend on the inner circumferential surface of the cylindrical wall portion 412b to the proximal side of (behind) the optically effective range r1 of the illumination lens 412 along the axial directions of the distal end section body 406a.

Here, the optically effective range r1 of the illumination lens 412 is a part positioned to the distal side of an emission end surface 411a of the light guide 411. In this manner, the function of the two-color molded product 413 is not lost by this rotation regulation portion 420.

The method of manufacturing the two-color molded product 413 is basically the same as that in the first embodiment.

Hereinafter, difference to the first embodiment will be described. In the present embodiment, as shown in FIG. 18, an outer shape of the illumination lens 412 is configured in an elliptical shape.

Further, the longitudinal directions of the ellipse of the illumination lens 412 is arranged in directions so as not to interfere with the other holes of the distal end section body 406a of the two-color molded product 413. The aforementioned other holes are a first hole (channel hole) 406a1 and a fourth hole 406a4.

As shown in FIG. 17, a primary sprue 422 and a primary molding pin point gate 422a to fill primary molding resin are arranged in a longitudinal side surface of the ellipse. Therefore, the rotation regulation portion 420 can ensure a sufficient space in the longitudinal directions of the ellipse of the illumination lens 412, as shown in FIG. 17 and FIG. 18. The part is formed in the inner circumferential surface of the cylindrical wall portion 412b of the illumination lens 412 in the longitudinal directions of the ellipse.

Due to this configuration, when the illumination lens 412 is molded in the primary molding by a primary-molding metal die, the rotation regulation portion 420 is formed in the inner circumferential surface of the cylindrical wall portion 412b of the illumination lens 412 as in the first embodiment. In this manner, the illumination lens 412 as the primary molded object is held in fit engagement with the insert body and the rotation regulation portion forming member of the movable insert of the movable-side metal die by molding shrink.

Subsequently, the primary-molding metal die rotates an unillustrated movable platen 180 degrees by rotating a rotation shaft of an unillustrated injection molding machine, with the illumination lens 412 held as in the first embodiment, after mold opening movement. By this rotation, the movable-side metal die on which the primary molded object 421 is placed and a secondary fixed metal die of a secondary-molding metal die are faced (opposed) to each other. In this state, the support member 416 is secondarily molded so as to be integrated with the circumference of the illumination lens 412 of the primary molded object 421. Simultaneously, the illumination lens 412 and the support member 416 are combined to form the two-color molded product 413.

In the present embodiment, the illumination lens 412 and the support member 416 are integrally molded into the two-color molded product 413 but are not limited hitherto. For example, the first lens 414a of the observation optical system 414 and the support member 416 may be integrally molded, or both the illumination lens 412 and the first lens 414a of the observation optical system 414 may be subjected to two-color molding integrally with the support member 416.

(Function/Effects)

Next, function of the configuration described above will be described.

According to the present embodiment, the longitudinal directions of the ellipse of illumination lens 412 is arranged so as not to interfere with the support member 416 or the other members in the distal end section 406 of the endoscope 401 except the optically effective range r1 of the illumination lens 412. A rotation regulation portion 420 is provided on the inner circumferential surface of the cylindrical wall portion 412b of the illumination lens 412 in the longitudinal directions.

In this manner, the two illumination lenses 412 rotate due to the injection pressure of molten resin at the time of molding the support member 416, and prevent the performance of the illumination lenses 412 from deterioration.

Further, each of the two illumination lenses 412 is prevented from rotating in circumferential directions of the illumination lens 412 by the rotation regulation portion 420 at the time of secondary molding. Accordingly, the outer shape of each of the illumination lenses 412 is prevented from projecting to the outer circumferential portion of the support member 416 by rotation or shifting of the illumination lenses 412.

By this configuration, illumination light emitted from emission end surface 411a of each of the light guides 411 is not scattered by part of the cylindrical wall portion 412b of each of the illumination lenses 412. The degree of freedom of the outer shape of a primary molded object can be improved, and the whole distal end section 406 of the endoscope 401 can be downsized.

Since each of the rotation regulation portions 420 is configured in concave shape in part of the inner circumferential surface of the cylindrical wall portion 412b of each of the two illumination lenses 412, the inner circumferential surface of each of the cylindrical wall portions 412b does not damage the function of inserting and fitly engaging the corresponding light guide 411 which emit light for illumination. Therefore, each of the rotation regulation portions 420 can be manufactured at the fit engagement part of the corresponding light guide 411 without degrading the performance of each of the light guides 411.

Further, each of the foregoing embodiments includes the subject matters of the invention described below and has the function and effects also described below.

According to a first aspect of the invention, a resin molded product includes that a primary molded object as an optical element which is molded by a primary molding die using a molding material having a light transmissibility; and a secondary molded object formed to be integrated with the primary molded object by a secondary molding die using a different molding material from the molding material of the primary molded object, the secondary molding die including at least a shared molding die which shares a part of the primary molding die, wherein the primary molded object includes a rotation regulation portion which makes a mutual concave-convex fit engagement at a joint portion between the primary molded object and a molding surface of the shared molding die, and which is configured to regulate rotation and shift of the primary molded object in circumferential directions about a center axis of the primary molded object.

Further, in the first aspect, secondary molding is performed by a secondary cavity which is formed between a male die and a second female die in a state that the rotation regulation portion of the first molded object and the male die are maintained in fit engagement with each other.

In this manner, even when the injection pressure of molten resin works unevenly to the primary molded object in the secondary molding, rotation and shifting of the primary molded object in the circumferential directions are prevented as maintained by the rotation regulation portion.

Therefore, even when the optically functional surface shape of the primary molded object has outer circumference having a disc shape, any slip does not occur in an interface between a second female die and the optically functional surface at the time of secondary molding, but the optical surface accuracy of the optical element of the primary molded object is maintained.

The primary molded object can maintain a designed configuration of the cavity which is formed by the male die holding the primary molded object and the second female die even when the primary molded object is a different shape other than the disc shape. In this manner, stable molding is available. Since the configuration of the cavity does not change, no thinned part is formed in an adjacent member, and accordingly, light shielding performance is not degraded.

Further, integral molding with the adjacent member can be achieved without exposing the optical element of the primary molded object to the exterior of the adjacent member and without thereby degrading optical performance by flares or ghosts.

According to a second aspect of the invention, the resin molded product described in the first aspect, wherein the primary molded object has at least a circular circumferential surface. In the resin molded product, a rotation regulation portion is a concave portion to be fitly engaged with a convex portion provided to extend from a part of a molding surface of the shared molding die to mold the circular circumferential surface toward the primary molded object side.

Further, in the second aspect, the convex portion is protruded from the circular circumferential surface of the molding surface to the primary molded object side at a part of a circular molding surface of the male die which molds the circular circumferential surface of the primary molded object. When the primary molded object as an optical element is primarily molded, a slip of the primary molded object in rotation directions about the center axis of the primary molded object is regulated by a fit engagement part between the convex portion of the circular molding surface of the male die and the concave portion at a part of the circular circumferential surface of the primary molded object.

In a third aspect of the invention, the resin molded product described in the first aspect wherein an optically functional plane of the optical element formed of two or more surfaces.

In a fourth aspect of the invention, the resin molded product described in the third aspect, the rotation regulation portion is provided at a place of the optical element other than an optically functional plane.

Further, in the fourth aspect, functions of the two-color molded product are not damaged by the rotation regulation portion by providing the rotation regulation portion at the place of the optical element other than the optically functional plane.

In a fifth aspect of the invention, the resin molded product described in the first aspect wherein the primary molded object includes an optical element body in which an optically functional plane is formed in two surfaces facing to each other, and a cylindrical wall portion having a cylindrical shape and connected to an outer circumferential part of the optical element body, and the rotation regulation portion is provided on(to) an inner circumferential surface of the cylindrical wall portion.

Further, in the fifth aspect, by providing the rotation regulation portion to the inner circumferential surface of the cylindrical wall portion which has the cylindrical shape and is connected to the outer circumferential part of the optical element body, the two surfaces of the optically functional plane of the primary molded object is not influenced by the rotation regulation portion, thereby to prevent functions of the two-color molded product from being eliminated.

In a sixth aspect of the invention, a resin molded product of an endoscope includes that an optical member as an optical element which is molded by a primary molding die using a molding material having a light transmissibility; and a distal end forming portion which is molded by a secondary molding die using a different molding material from the molding material of the optical member, the secondary molding die including at least a shared molding die shared with the primary molding die, and which is integrated with the optical member, the distal end forming portion forming a distal end section of the endoscope, wherein the optical member includes a rotation regulation portion which makes a mutual concave-convex fit engagement at a joint portion between the optical member and a molding surface of the shared molding die, and which is configured to regulate a slip of the optical member in rotation directions about a center axis of the optical member.

In a seventh aspect of the invention, an endoscope uses the resin molded product for the endoscope described in the sixth aspect.

In an eighth aspect of the invention, a method of manufacturing a resin molded product, includes that a primary molding step of molding a primary molded object as an optical element by a primary molding die using a molding material which has a light transmissibility; a mold opening step of performing mold opening of the primary molding die; and a secondary molding step of molding a secondary molded object by a secondary molding die after the mold opening step using a different molding material from the primary molding material, the secondary molding die including at least a shared molding die to be shared with the primary molding die, to thereby integrate the primary molded object and the secondary molded object, wherein the primary molding step is performed in a state in which a slip of the primary molded object is regulated in rotation directions about a center axis of the primary molded object by making a mutual concave-convex fit engagement maintained at a joint portion between the primary molded object and a molding surface of the shared molding die, and the secondary molding step is performed in a state that the concave-convex fit engagement is maintained at the joint portion.

Further in the eighth aspect, when the primary molded object is molded during the primary molding step, the mutual concave-convex fit engagement is made at the joint portion between the primary molded object and the molding surface of the shared molding die. In this manner, with the slip of the primary molded object being regulated in the rotation directions about the center axis of the primary molded object, the primary molded object is primarily molded, and the secondary molding step is performed with the concavo-convex fit engagement being maintained at the joint portion.

In this manner, even when an injection pressure of molten resin acts unevenly on the primary molded object at the time of the secondary molding, the joint portion between the primary molded object and the molding surface of the shared molding die is maintained in fit engagement. Therefore, the primary molded object is not any slip in the rotation directions about the center axis of the primary molded object.

Therefore, any slip does not occur at the interface with the optically functional plane which holds the primary molded object in the secondary molding, even if the shape of an engagement maintaining part between the primary molded object and the molding surface of the shared molding die is limited to a shape rotational-axially symmetrical. Accuracy of the optically functional plane of the optical element obtained by the primary molding can be maintained.

Even when the outer shape of the optical element is an asymmetrical shape different from a shape rotational-axially symmetrical, a designed configuration of the cavity formed at the joint portion between the molding surface of the shared molding die holding the optical element and the primary molded object can be maintained. Since stable molding is therefore possible and the configuration of the cavity does not change, no thinned part is formed in an adjacent member. In this manner, the optical element and the adjacent member can be integrally molded without degrading light shielding performance, without exposing the optical element to the exterior of the adjacent member and without thereby degrading optical performance due to flares or ghosts.

In a ninth aspect of the invention, a molding die for a resin molded product includes that a primary molding die which is configured to mold a primary molded object as an optical element using a molding material having a light transmissibility; and a secondary molding die which includes at least a shared molding die to be shared with the primary molding die, and which is configured to mold a secondary molded object integrated with the primary molded object using a different molding material from the molding material of the primary molded object, wherein the shared molding die includes a rotation regulation portion forming member which makes a mutual concave-convex fit engagement at a joint portion between the primary molded object and a molding surface of the shared molding die, to thereby regulate a slip of the primary molded object in rotation directions about a center axis of the primary molded object.

In a tenth aspect of the invention, the molding die for the resin molded product described in the ninth aspect wherein the molding surface of the primary molding die has at least a circumferential surface, and the rotation regulation portion forming member is a convex portion protruded from a part of the circumferential surface of the molding surface of a shared molding die toward the primary molded object side.

In an eleventh aspect of the invention, the molding die for the resin molded product according to the tenth aspect wherein the rotation regulation portion forming member is a part of an insert inserted into the shared molding die.

According to the invention, the primary molded object is formed by the primary molding. The primary molded object is provided with the rotation regulation portion, which is configured to regulate the slip of the primary molded object in the rotation directions about the center axis of the primary molded object, at a fit engagement maintaining part of a joint portion with the molding surface of the shared molding die. The rotation regulation portion suppresses rotation of the primary molded object even if the injection pressure of molten resin acts unevenly on the primary molded object during the secondary molding. By preventing this rotation, molding stability and shielding performance can be ensured also in the adjacent member obtained by the secondary molding without degrading the quality of the primary molding object during the secondary molding The invention can provide a resin molded product in which an optical element of a primary molded object and an adjacent member obtained by a secondary molding integrated with each other, a manufacturing method of the same, and a molding die for the resin molded product.

The invention includes features summarized below.

An endoscope uses a resin molded product, comprising:

an optical member as an optical element which is molded by a primary molding die using a molding material having a light transmissibility;

a distal end forming portion which is molded by a secondary molding die using a different molding material from the molding material of the optical member, the secondary molding die including at least a shared molding die shared with the primary molding die, and which is integrated with the optical member, the distal end forming portion forming a distal end section of the endoscope; wherein the optical member includes a rotation regulation portion which makes a mutual concave-convex fit engagement at a joint portion between the optical member and a molding surface of the shared molding die, and which is configured to regulate a slip of the optical member in rotation directions about a center axis of the optical member.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A molded product, comprising:
a transparent resin object having a lens portion and a skirt portion, the lens portion having an optical axis and an optically effective range along the optical axis, the skirt portion being located outside of the optically effective range as viewed along the optical axis, the skirt portion having radially inner and outer surfaces and a slot formed in the inner surface such that it is located outside of the optically effective range of the lens portion; and
an opaque resin object integrally coupled to an outer surface of the transparent resin object.

2. The molded product of claim 1, wherein the slot extends axially parallel to the optical axis.

3. The molded product of claim 2, wherein the inner surface of the skirt portion is rotationally symmetrical except for the slot.

4. The molded product of claim 1, wherein the lens portion is defined between opposed optical surfaces.

5. The molded product of claim 1, wherein the optically effective range is defined by the opposed optical surfaces.

6. The molded product of claim 5, wherein both of the optical surfaces are curved surfaces.

7. The molded product of claim 5, wherein one of the optical surfaces is planar and the other is curved.

8. An endoscope, comprising:
an elongated flexible tube having a proximal and a distal end;
an optical system located in the distal end of the flexible tube, the optical system including:
a transparent resin object having a lens portion and a skirt portion, the lens portion having an optical axis and an optically effective range along the optical axis, the skirt portion being located outside of the optically effective range as viewed along the optical axis, the skirt portion having radially inner and outer surfaces and a slot formed in the inner surface such that it is located outside of the optically effective range of the lens portion; and an opaque resin object integrally coupled to an outer surface of the transparent resin object.

9. A molding die for molding a resin product, the die comprising:

first, second and third die halves, the first die half moving between a first position where it cooperates with at least the second die half to form a primary die and a second position where it cooperates with at least the third die to form a secondary die;

the primary die defining a first cavity in which a transparent molded object may be molded around a member which forms part of the first die half and which is rotationally symmetrical about axis, the member having a circumference which extends around an entire periphery of the rotationally symmetrical member and which is centered on the axis, the first die half having a rotation prevention member extending radially from the rotationally symmetrical member but not extending around the entire circumference of the rotationally symmetrical member, the rotation prevention member forming a corresponding indentation in the transparent resin object when the transparent resin object is molded around the rotationally symmetrical member; and the secondary die having a second cavity in which an opaque resin object may be molded around a periphery of the transparent resin object, the rotation prevention member and the indentation on the transparent resin object cooperating to prevent the transparent resin object from rotating relative to the rotationally symmetrical member as the opaque resin object is molded around the periphery of the transparent resin object.

10. The molding die of claim 9, wherein the rotation prevention member is part of a removable insert forming part of the first die half.

11. The molding die of claim 9, wherein the transparent resin object has a lens portion and a skirt portion, the lens portion having an optical axis and an optically effective range along the optical axis, the skirt portion being located outside of the optically effective range as viewed along the optical axis, the skirt portion having radially inner and outer surfaces and the indentation is formed in the inner surface such that it is located outside of the optically effective range of the lens portion.

12. A method for molding a resin product, the method comprising:

molding a transparent resin object in a first die which includes first and second die halves, the first die half including a member which is rotationally symmetrical about an axis and around which the transparent resin object is molded, the member having a circumference which extends around an entire periphery of the rotationally symmetrical member and which is centered on the axis, a rotation prevention member extending radially from the rotationally symmetrical member but not extending around the entire circumference of the rotationally symmetrical member, the rotation prevention member forming a corresponding indentation in the transparent resin object when the transparent resin object is molded around the rotationally symmetrical member;

opening the first die;

moving the first die half, and with it the transparent resin object, into a operative relationship with at least a third die half to form a second die; and using the second die to mold an opaque resin object around a periphery of the transparent resin object, the rotation prevention member and the indentation on the transparent resin object cooperating to prevent the transparent resin object from rotating relative to the rotationally symmetrical member as the opaque resin object is molded around the periphery of the transparent resin object.

13. The method of claim 12, wherein the rotationally symmetrical member is a cylinder.

14. The method of claim 13, wherein the cylinder and the rotation prevention member are separate pieces.

15. The method of claim 13, wherein the cylinder and the rotation prevention member are part of a removable insert forming part of the first die half.

16. The method of claim 13, wherein the transparent molded object comprises a lens portion and a skirt portion, the lens portion having an optical axis and an optically effective range along the optical axis, the skirt portion being located outside of the optically effective range as viewed along the optical axis, the skirt portion having radially inner and outer surfaces and a slot formed in the inner surface such that it is located outside of the optically effective range of the lens.

\* \* \* \* \*